US009880138B1

(12) United States Patent
Hall et al.

(10) Patent No.: US 9,880,138 B1
(45) Date of Patent: Jan. 30, 2018

(54) MEDICAL TOILET FOR DIAGNOSING DISEASE AND USE WITH DISEASE SNIFFING ANIMAL

(71) Applicants: David R. Hall, Provo, UT (US); Joe Fox, Spanish Fork, UT (US); Terrece Pearman, Draper, UT (US)

(72) Inventors: David R. Hall, Provo, UT (US); Joe Fox, Spanish Fork, UT (US); Terrece Pearman, Draper, UT (US)

( * ) Notice: Subject to any disclaimer, the term of this patent is extended or adjusted under 35 U.S.C. 154(b) by 0 days.

(21) Appl. No.: 15/271,485

(22) Filed: Sep. 21, 2016

(51) Int. Cl.
*G01N 33/00* (2006.01)
*E03D 9/052* (2006.01)

(52) U.S. Cl.
CPC ......... *G01N 33/0001* (2013.01); *E03D 9/052* (2013.01)

(58) Field of Classification Search
CPC .............................. G01N 33/0001; E03D 9/052
See application file for complete search history.

(56) References Cited

U.S. PATENT DOCUMENTS

| | | | | |
|---|---|---|---|---|
| 4,944,045 A * | 7/1990 | Agelatos | ................. | E03D 9/052 4/213 |
| 5,029,346 A * | 7/1991 | Fernald, Sr. | ............ | E03D 9/052 4/213 |
| 5,073,500 A * | 12/1991 | Saito | ................... | A61B 5/14507 4/300 |
| 5,454,122 A * | 10/1995 | Bergeron | ................. | E03D 9/052 4/213 |
| 5,625,911 A * | 5/1997 | Nakayama | ........... | A61B 10/007 4/661 |
| 5,720,054 A * | 2/1998 | Nakayama | ........... | A61B 10/007 4/420 |
| 6,019,862 A * | 2/2000 | Cardwell | ............. | C04B 37/001 156/62.2 |

(Continued)

FOREIGN PATENT DOCUMENTS

EP 2545847 A1 * 1/2013 ............... A61B 5/00

OTHER PUBLICATIONS

McCulloch, Michael, et al. "Diagnostic accuracy of canine scent detection in early-and late-stage lung and breast cancers." Integrative cancer therapies5.1 (2006): 30-39.*
Cornu, Jean-Nicolas, et al. "Olfactory detection of prostate cancer by dogs sniffing urine: a step forward in early diagnosis." European urology 59.2 (2011): 197-201.*
Bjartell, Anders S. "Dogs sniffing urine: a future diagnostic tool or a way to identify new prostate cancer markers?." European urology 59.2 (2011): 202-203.*
Taverna, Gianluigi, et al. "Olfactory system of highly trained dogs detects prostate cancer in urine samples." The Journal of urology 193.4 (2015): 1382-1387.*

(Continued)

*Primary Examiner* — Harshad R Patel
*Assistant Examiner* — Punam Roy

(57) ABSTRACT

Many diseases are difficult to diagnose or present with no symptoms that would suggest that medical diagnosis is needed until significant bodily damage has occurred. We disclose a medical toilet that may be used to diagnose disease. The toilet comprises a conduit through which volatile organic compounds travel from the toilet bowl to the environment outside the toilet. The invention includes methods that comprise the steps of training an animal to identify the scent of bodily waste collected from a user that is afflicted with a defined disease. A user's bodily waste is deposited into the medical toilet and the animal is then exposed to the volatile organic compounds traveling through the conduit on the medical toilet. The animal performs an act that signals that the animal has perceived the smell associated with the disease. Thus, we disclose a novel device for diagnosing disease and methods of user thereof.

6 Claims, 12 Drawing Sheets

(56) References Cited

U.S. PATENT DOCUMENTS

| | | | | |
|---|---|---|---|---|
| 6,088,845 | A * | 7/2000 | Estrada | E03D 9/05 4/306 |
| 6,209,146 | B1 * | 4/2001 | Gonzalez | E03D 9/05 4/209 R |
| 6,212,698 | B1 * | 4/2001 | Stingley | A61B 10/007 4/144.1 |
| 6,279,173 | B1 * | 8/2001 | Denzin | E03D 9/05 4/213 |
| 6,370,702 | B1 * | 4/2002 | Iddings, Sr. | E03D 9/05 4/213 |
| 6,496,986 | B1 * | 12/2002 | Lumsden | E03D 9/05 4/213 |
| 6,966,840 | B2 * | 11/2005 | Nelson | G08B 21/12 446/175 |
| 7,987,527 | B1 * | 8/2011 | Shumaker | E03D 9/052 4/213 |
| 9,499,966 | B2 * | 11/2016 | Darnell | E03D 9/05 |
| 9,592,034 | B2 * | 3/2017 | Hall | A61B 10/007 |
| 9,671,343 | B1 * | 6/2017 | Hall | G01N 21/6428 |
| 2001/0031913 | A1 * | 10/2001 | Ito | A61B 5/0002 600/300 |
| 2005/0261605 | A1 * | 11/2005 | Shemer | A61B 10/007 600/573 |
| 2008/0256696 | A1 * | 10/2008 | Walsmley | A61B 10/0038 4/420 |
| 2009/0216099 | A1 * | 8/2009 | Kim | A61B 5/022 600/345 |
| 2016/0000378 | A1 * | 1/2016 | Hall | A61B 5/0075 702/19 |
| 2016/0345539 | A1 * | 12/2016 | Mark-Danieli | A01K 1/031 |
| 2017/0204595 | A1 * | 7/2017 | Hall | E03D 9/052 |
| 2017/0242004 | A1 * | 8/2017 | Hanson | G01N 21/77 |

OTHER PUBLICATIONS

Horowitz, Alexandra, Julie Hecht, and Alexandra Dedrick. "Smelling more or less: Investigating the olfactory experience of the domestic dog." Learning and motivation 44.4 (2013): 207-217.*

Cornu, Jean-Nicolas, and Olivier Cussenot. "Reply to Giuseppe Lippi's Letter to the Editor re: Jean-Nicolas Cornu, Géraldine Cancel-Tassin, Valérie Ondet, et al. Olfactory Detection of Prostate Cancer by Dogs Sniffing Urine: A Step Forward in Early Diagnosis. Eur Urol 2011; 59: 197-201." European Urology60.4 (2011): e30.*

Walczak, Marta, et al. "Impact of individual training parameters and manner of taking breath odor samples on the reliability of canines as cancer screeners." Journal of Veterinary Behavior: Clinical Applications and Research 7.5 (2012): 283-294.*

Matsumura, Koichi, et al. "Urinary volatile compounds as biomarkers for lung cancer: a proof of principle study using odor signatures in mouse models of lung cancer." PLoS One 5.1 (2010): e8819.*

Bomers, Marije K., et al. "Using a dog's superior olfactory sensitivity to identify Clostridium difficile in stools and patients: proof of principle study." (2012): e7396.*

Willis, Carolyn M., et al. "Olfactory detection of human bladder cancer by dogs: proof of principle study." Bmj 329.7468 (2004): 712.*

Y. Oh, Y. Lee, J. Heath and M. Kim, "Applications of Animal Biosensors: A Review," in IEEE Sensors Journal, vol. 15, No. 2, pp. 637-645, Feb. 2015.*

* cited by examiner

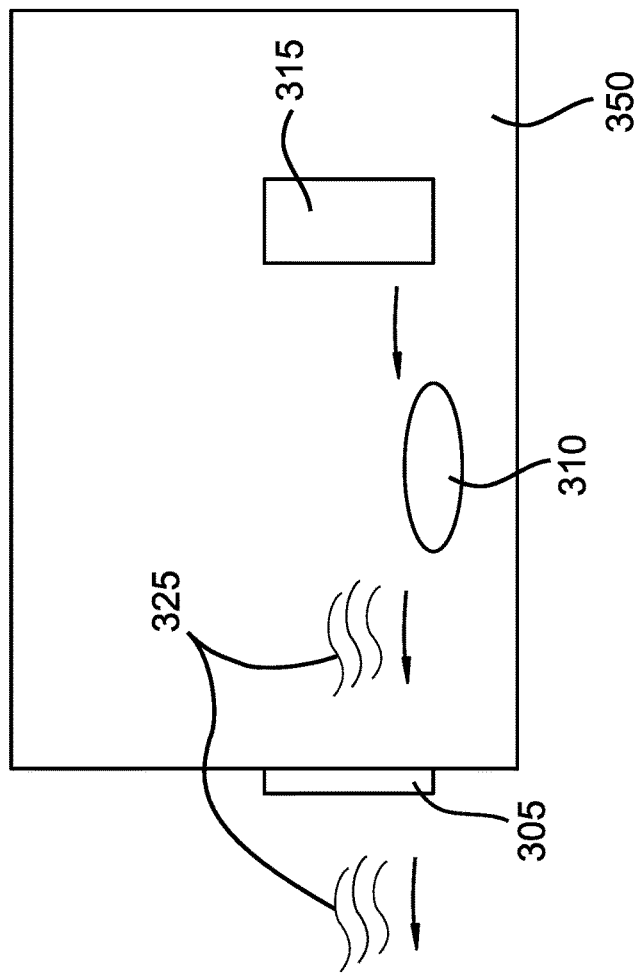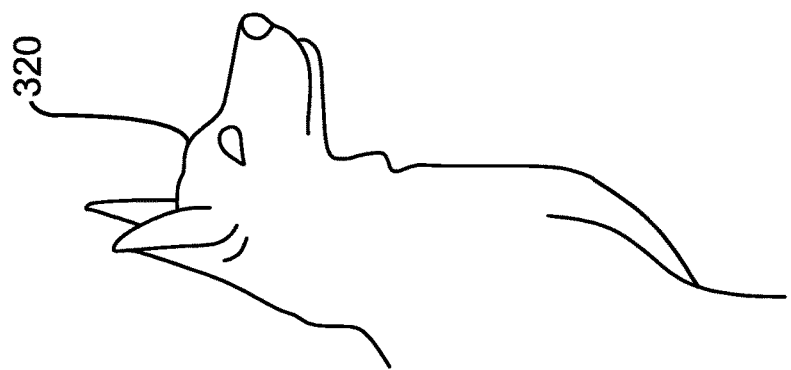
FIG. 3A

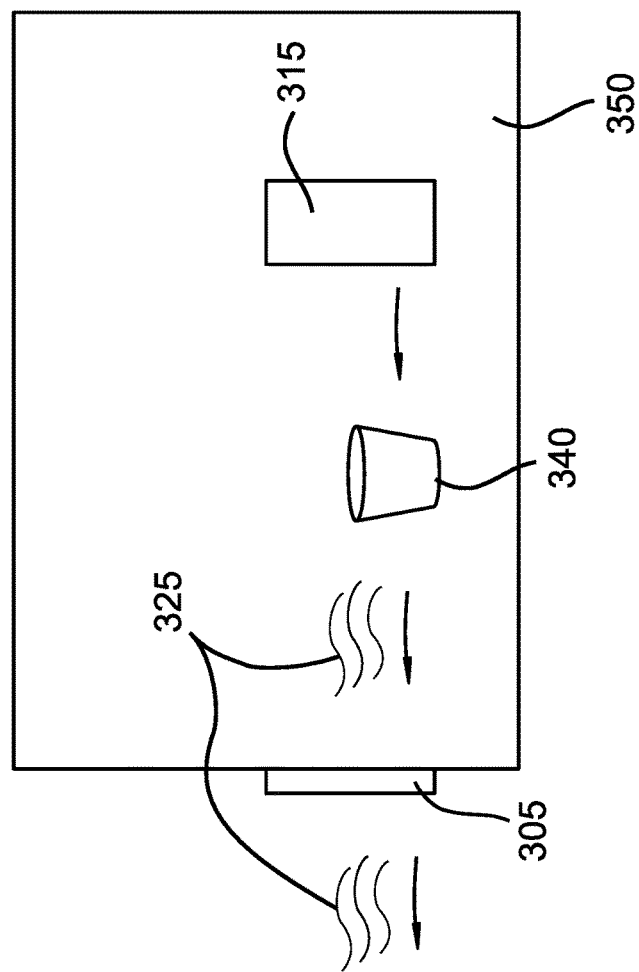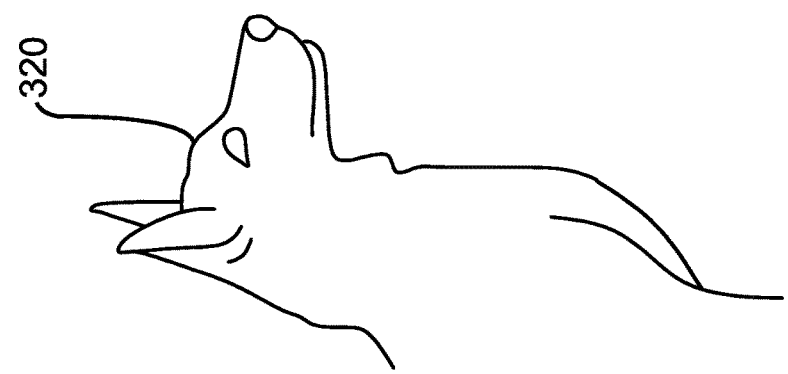
FIG. 3B

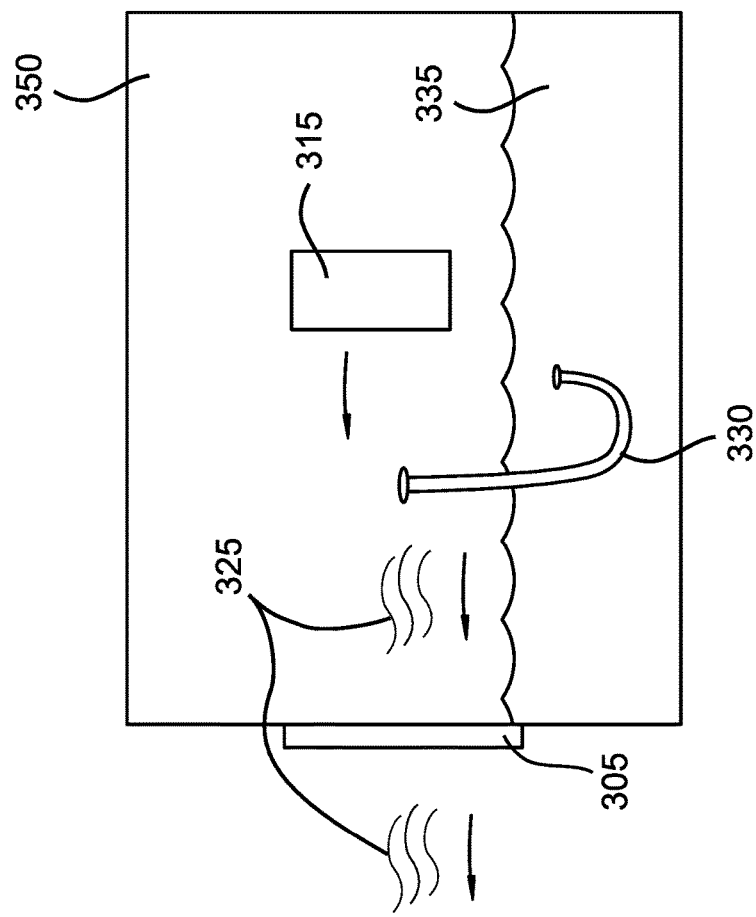
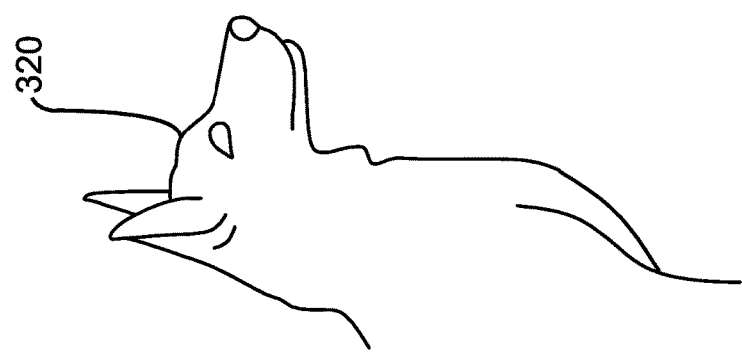
FIG. 3C

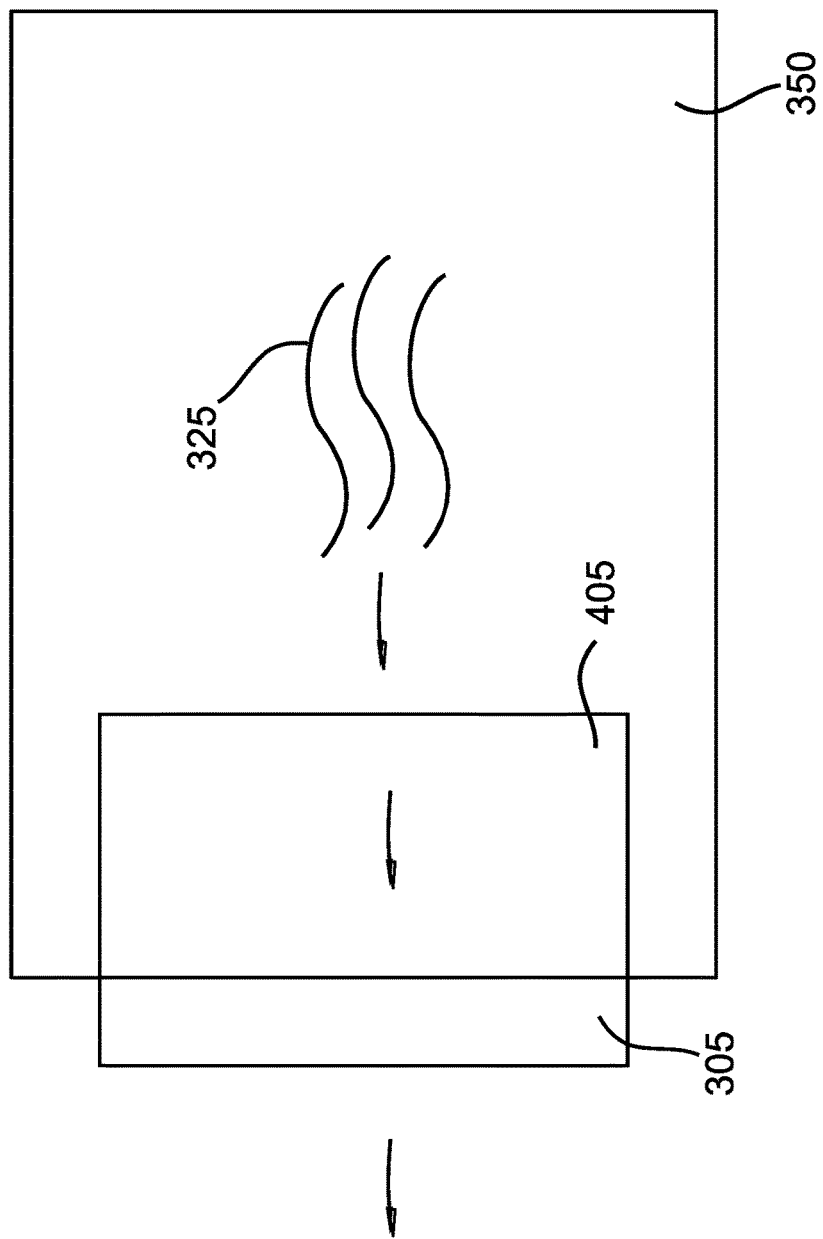

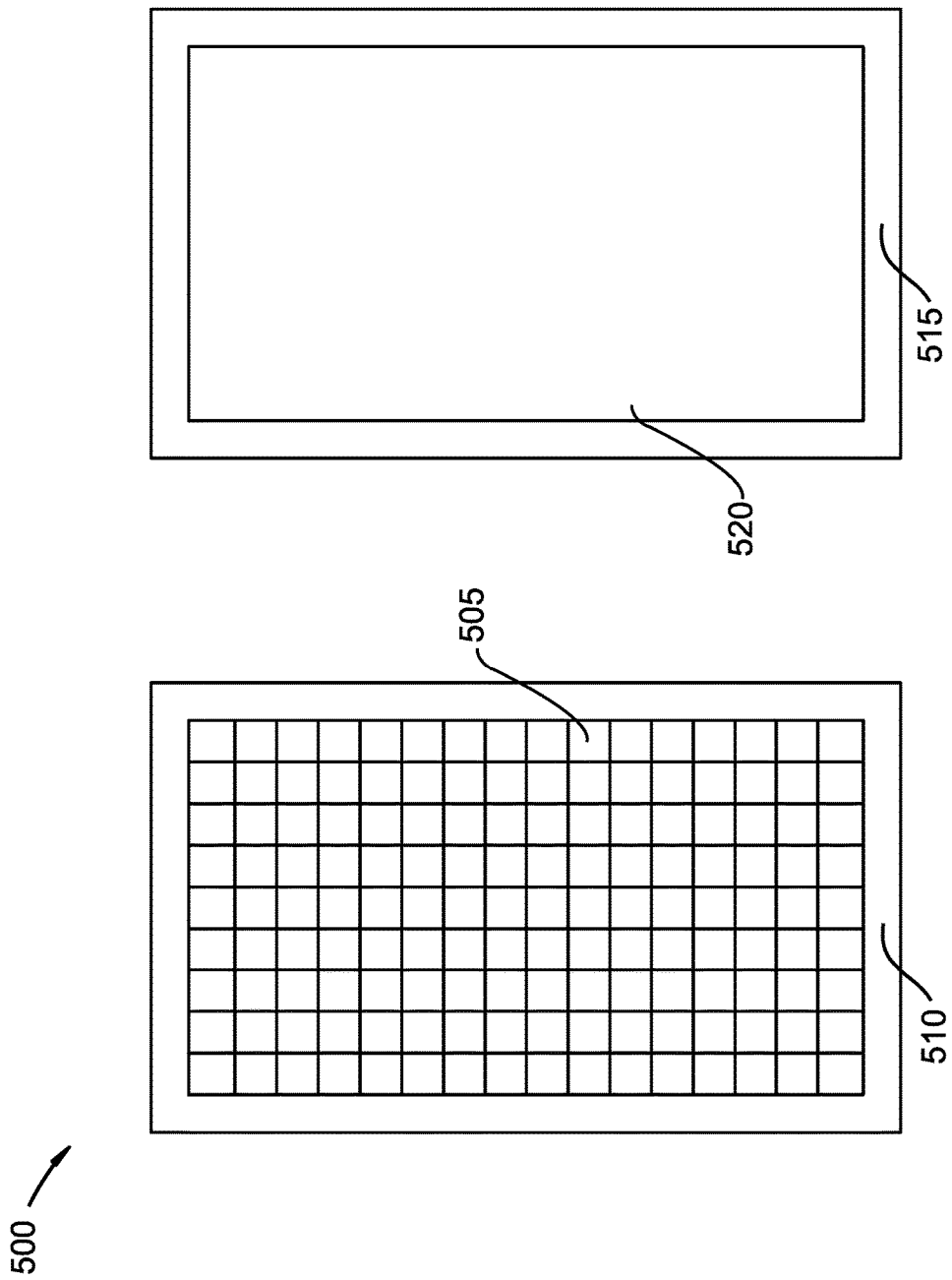

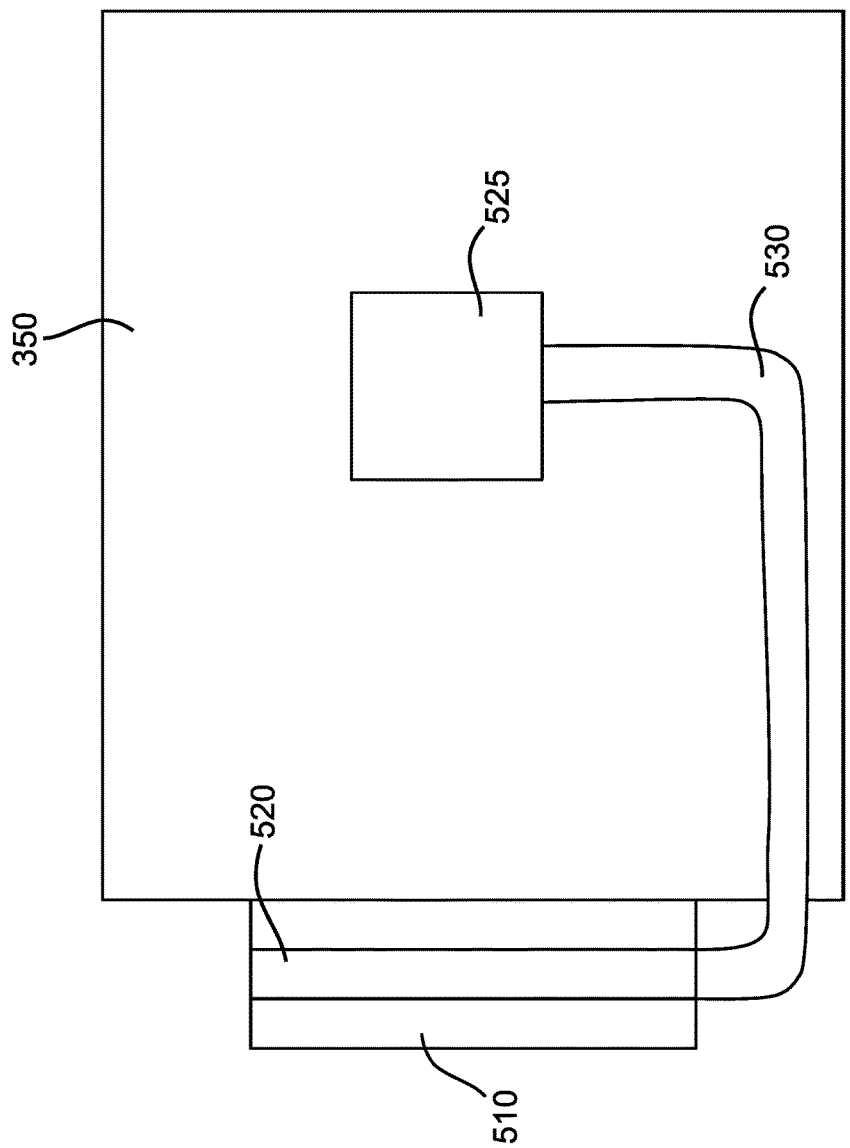

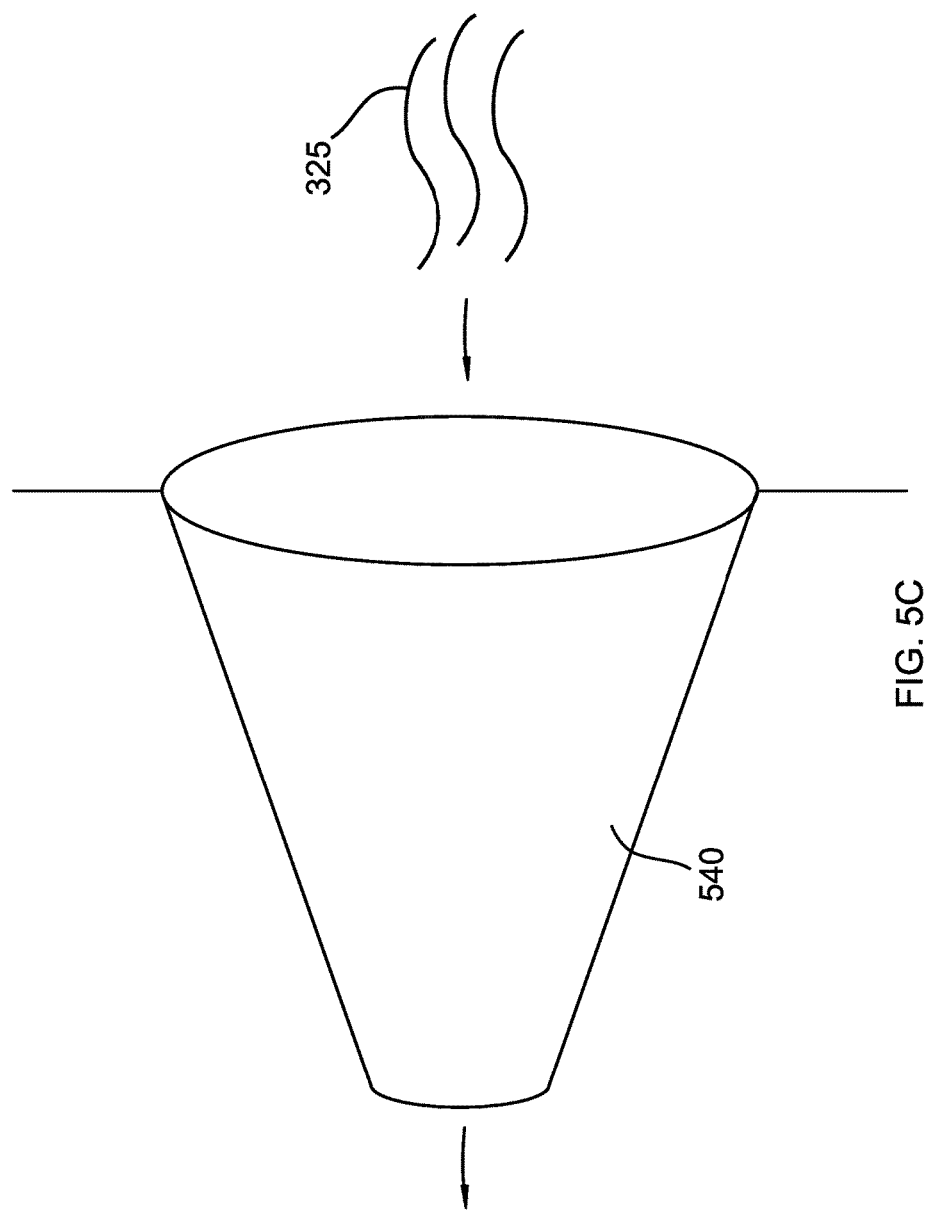

MEDICAL TOILET FOR DIAGNOSING DISEASE AND USE WITH DISEASE SNIFFING ANIMAL

BACKGROUND

Field of the Invention

This invention relates to a device for diagnosing disease and use thereof.

Background of the Invention

Many animals have heightened senses relative to humans. In fact, humans have used the relatively enhanced ability to see, hear, and smell of animals to perform tasks for hundreds of years. In particular, dogs have been used for their enhanced sense of smell to assist in tasks that include hunting, protecting livestock from predators, searching for specific humans, and detecting illegal substances. More recently, evidence has been reported that dogs have predicted seizures before they happened and identified cancer. Other organisms, including rats, mice, and insects show behavior that suggests they can identify a diseased organism.

It is unclear what substances animals smell when they identify disease. Furthermore, studies show that a variety of biological substances collected from a diseased human emit substances that animals distinguish from those of healthy humans. Reports of animals identifying disease include those in which the animal evaluated feces, urine, blood, and exhaled breath. Each of these biological substances emit volatile organic compounds (VOCs). It is likely that the biological samples the animals identify as those from a diseased human emit a plurality of different VOCs. It may be this combination that the animal perceives as the scent of disease. By smelling the combination of molecules that collectively identify disease, the animal may be able to diagnose with more sensitivity and specificity than available laboratory assays. Part of the reason the animal's sense of smell may be a more accurate diagnostic tool may be that laboratory assays often detect a single molecule. In contrast, an accurate diagnosis may best be obtained by detecting the simultaneous presence of multiple VOCs.

BRIEF SUMMARY OF THE INVENTION

Some diseases do not present with symptoms until the disease has done significant damage. Consequently, these diseases often go undiagnosed until later in the disease process. In addition, there is no reliable diagnostic test for some diseases. A diagnostic medical device and method of its use is needed that is convenient to use, even at home. In particular, such a device is needed for diseases that do not have a reliable diagnostic test available.

As an answer to these problems, we disclose a medical toilet that includes a scent dispenser. The scent dispenser may be positioned on a side of the medical toilet and is in communication with the toilet bowl within the medical toilet. The scent dispenser comprises a conduit through which air from within the toilet bowl may travel to the environment outside the medical toilet. When bodily waste from the user is deposited into the toilet bowl, the bodily waste emits volatile organic compounds (VOCs). Mechanisms within the medical toilet direct the air within the toilet bowl toward and through the scent dispenser. An animal is positioned outside the medical toilet in the vicinity of the scent dispenser. According to the invention, the animal has been trained to differentiate the scent of VOCs that emit from bodily waste that was collected from a user with a defined disease from that collected from a user that is not afflicted with the defined disease. The animal performs an act which signals to an observer that the animal has perceived the scent of VOCs associated with the disease. In doing so, the user receives a diagnosis that indicates that the user may require additional health care.

BRIEF DESCRIPTION OF THE DRAWINGS

FIG. 3A is a schematic drawing of an embodiment of the medical toilet.

FIG. 3B is a schematic drawing of an embodiment of the medical toilet.

FIG. 3C is a schematic drawing of an embodiment of the medical toilet.

FIG. 4 is a schematic drawing of an embodiment of a scent dispenser and blower.

FIG. 5A is a perspective view of an embodiment of the scent dispenser.

FIG. 5B is a schematic drawing of a side view of the embodiment of the scent dispenser of FIG. 5A on an embodiment of the medical toilet.

FIG. 5C is a side view of an embodiment of the scent dispenser.

DETAILED DESCRIPTION OF THE INVENTION

Definitions

Figure 1:
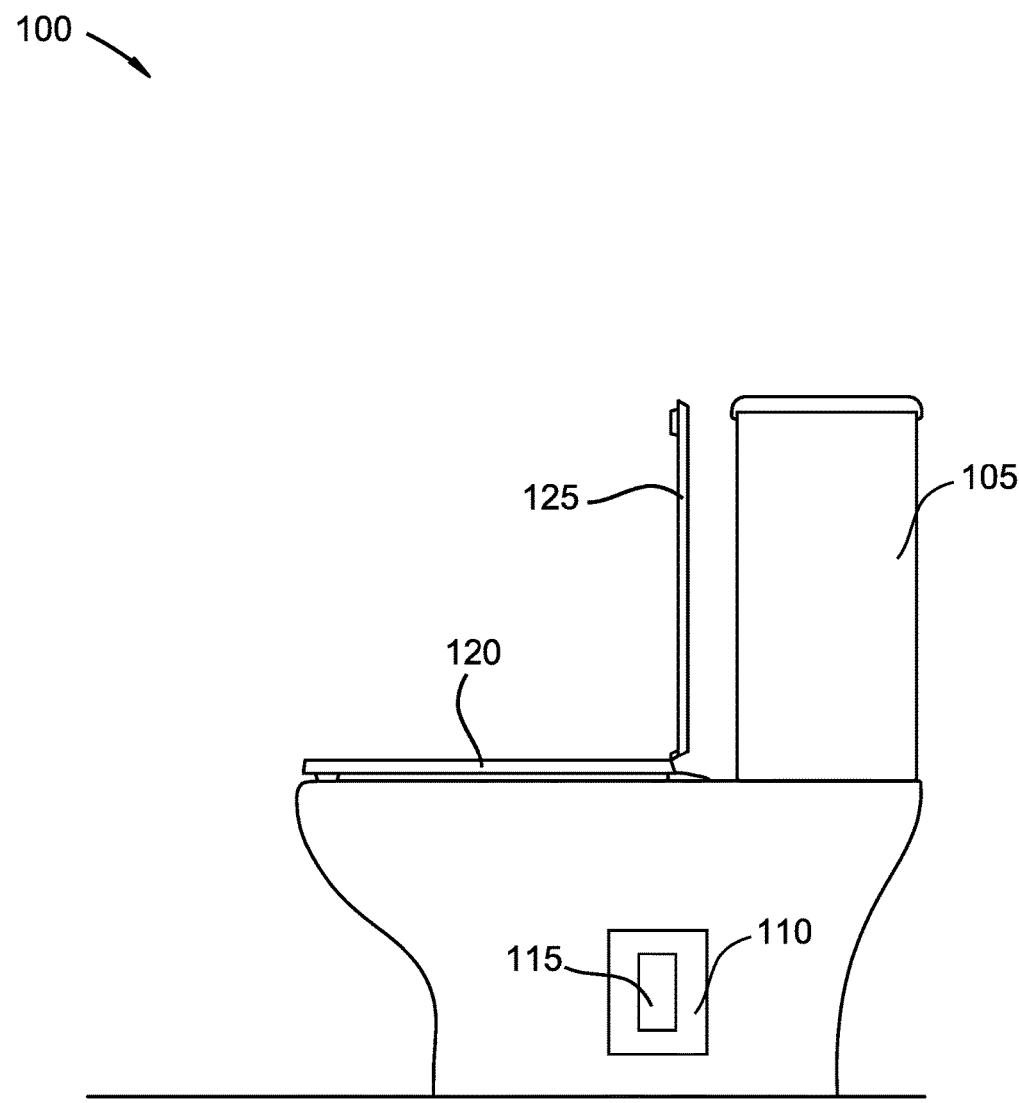
FIG. 1 is a side view of a medical toilet with an embodiment of the scent dispenser.

Toilet, as used herein, means a device that may be used to collect one or more biological waste products of a user.

User, as used herein, means a human or animal that deposits bodily waste into an embodiment of the toilet disclosed herein.

Bodily waste, as used herein, means any one or combination of urine, feces, vomit, sputum, blood, seminal fluid, tears, nasal mucus, gastrointestinal tract mucus, urogenital tract mucus, saliva, exhaled breath, or sweat from the body of a user.

Animal, as used herein, means non-human members of kingdom Animalia, including vertebrates, invertebrates, insects, and marine organisms.

Disease, as used herein, means any disorder of structure or function in the body or a human or animal, whether or not the disorder presents with signs or symptoms. As used herein, the term disease includes non-infectious disorders and disorders caused by physical injury.

Diseases that may be diagnosed according to the methods disclosed herein and using the medical toilet disclosed herein include, but are not limited to, colon adenoma, colon carcinoma, colon adenocarcinoma, colorectal adenoma, colorectal carcinoma, colorectal adenocarcinoma, bladder carcinoma, bladder adenocarcinoma, liver adenoma, liver carcinoma, liver adenocarcinoma, esophageal adenoma, esophageal carcinoma, esophageal adenocarcinoma, stomach adenoma, stomach carcinoma, stomach adenocarcinoma, pancreatic adenoma, pancreatic carcinoma, pancreatic adenocarcinoma, lung cancer, mouth cancer, throat cancer, inflammatory bowel disease, urinary tract infection, gastric ulcer, diabetes, hyperglycemia, hypoglycemia, impending seizure, and impending migraine.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Disclosed herein is a medical toilet, which comprises a medical device used to diagnose disease in a user. The toilet differs from those used simply to collect and dispose of urine and feces at least because it includes a scent dispenser. The scent dispenser acts as a conduit through which volatile organic compounds (VOCs) may travel from the environment inside of the toilet, for example, the toilet bowl, to the environment outside the toilet, for example, the room air.

In some embodiments, the medical toilet comprises a blower which functions to move air surrounding the bodily waste that a user has deposited into the medical toilet, along with the VOCs contained therein, toward the scent dispenser. The blower may comprise a fan, air pump, or other device known in the art which may move air in a defined direction. In some embodiments, the blower is positioned within the toilet bowl approximately opposite the toilet bowl from the scent dispenser. This configuration results in the blower creating an air current that moves air within the toilet bowl from a point approximately opposite the scent dispenser, over and around the biological waste which is positioned between the blower and the scent dispenser, and through the scent dispenser into the environment outside of the medical toilet.

In another embodiment, the blower is located on the same side of the toilet bowl as the scent dispenser. Rather than create positive pressure to push air away from the blower and toward the scent dispenser, the blower of this embodiment creates negative pressure and pulls or sucks air toward the scent dispenser. Thus, the air surrounding the biological waste that within the toilet bowl, along with the VOCs contained therein, is pulled toward the scent dispenser. The air and VOCs then travel through the scent dispenser and into the environment outside the toilet.

Some embodiments may comprise a length of tubing in connection with the scent dispenser. A user may exhale into a first end of the tubing, thus transferring the user's breath to the scent dispenser.

The scent dispenser may comprise of an opening on the side of the medical toilet. FIG. 1 illustrates an embodiment in which the medical toilet 100 appears much like a traditional toilet with a seat 120, lid 125, and tank 105. However, FIG. 1 further illustrates an embodiment of a scent dispenser on toilet 100 which comprises a frame 110 surrounding a screen 115. Frame 110 may be constructed of a variety of materials including, but not limited to, one or more of metal, porcelain, rubber or rubberized materials, plastics that comprise of any of a variety of polymers and copolymers known in the art, glass, silicone, and ceramic. Frame 110 may be constructed of any of a variety of materials that are water resistant so as to not be damaged by exposure to toilet water. Frame 110 may include a gasket constructed of one or more of rubber, rubberized material, plastics that comprise of any of a variety of polymers and copolymers known in the art, or other materials known to prevent liquid leakage.

Frame 110 surrounds screen 115 which may be constructed of a porous material through which air and accompanying VOCs may travel. Screen 115 may be constructed from one or more of metal, rubber or rubberized materials, plastics that comprise of any of a variety of polymers and copolymers known in the art, and filter paper.

For use in diagnosis of disease, an animal is positioned near the toilet and a user deposits bodily waste into the toilet bowl. The blower is activated through mechanisms known in the art which include the use of motion sensors which would cause a signal to be transmitted to the blower when biological waste passes by the sensor. Alternatively, the user, or possibly even the animal, may turn the blower on or off by pressing a button or flipping a switch.

The user deposits bodily waste into the toilet through actions which include urinating or defecating into the toilet, vomiting into the toilet, coughing up sputum into the toilet, and depositing mucus into the toilet. A user may deposit nasal mucus and sputum into the toilet by coughing or blowing the user's nose into a tissue and tossing the tissue into the toilet.

An animal may be trained to sniff the scent dispenser in response to a command or signal which the user gives the animal when the user desires the animal to assess the presence of disease in the user. Alternatively, the animal may simply be trained that the scent dispense is something that the animal should sniff and do so when placed in the proximity of the toilet. Furthermore, the animal may be an insect that is placed in a container. The container may be attached to or placed in the vicinity of the scent dispenser avoiding any need to train the animal to approach the scent dispenser.

The animal must also be trained to identify a disease by the smell of bodily waste collected from a user who has that disease and to differentiate this from scents emitted by bodily waste collected from users who do not have the disease. Furthermore, the animal must be trained to perform a behavior that functions as a signal to the user that the animal has detected the scent of disease in the user's bodily waste. Methods of training an animal to identify a sample of bodily waste that was obtained from a diseased organism as well as methods to train the animal to provide a signal to communicate upon perceiving a particular scent are known in the art and within the scope of the methods disclosed herein.

Figure 2:
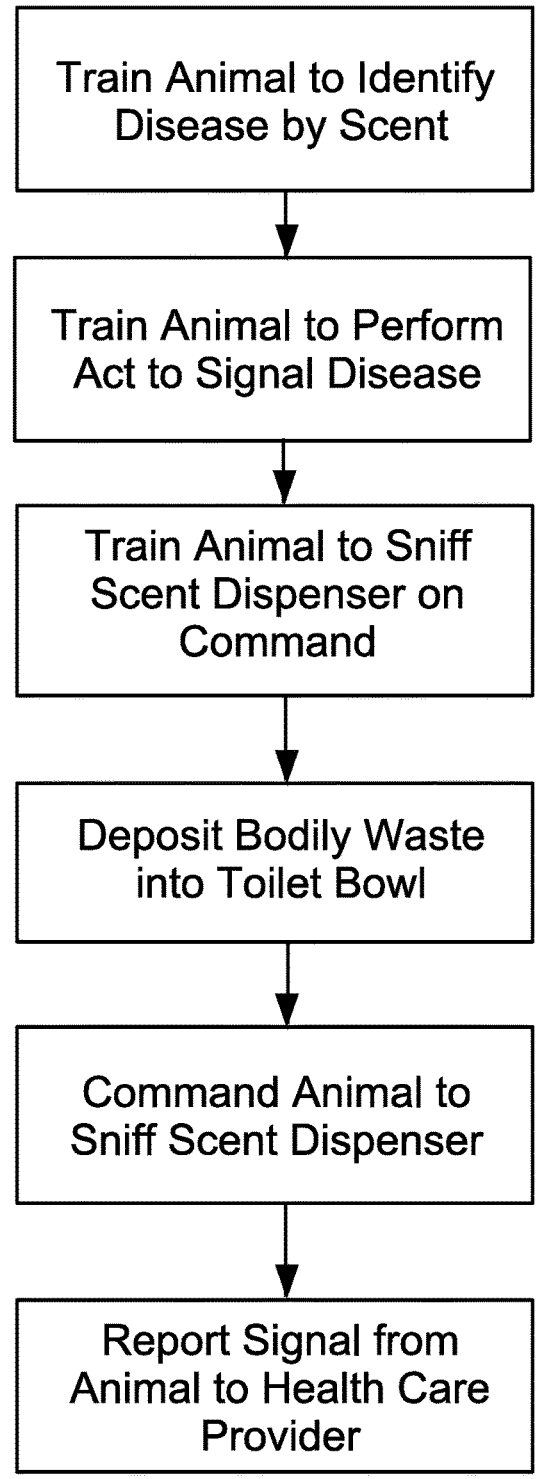
FIG. 2 is a flow chart illustrating a method of using the medical toilet of FIG. 1 comprising a trained animal.

FIG. 2 is a flow chart that illustrates an embodiment of a method of using the medical toilet disclosed herein. In this embodiment, the animal is first trained to identify bodily waste collected from a user and differentiate whether the user is afflicted with a particular disease or not. The animal is trained to perform a defined act upon perceiving the scent associated with the disease. Next the animal is trained to sniff the scent dispenser on command. The animal is now ready to participate in diagnosis of a user. Not that in some embodiments, the step of, training to sniff the scent dispenser on command may not be necessary. The animal is then brought to the medical toilet and a user's bodily waste is deposited into the toilet. The animal is given the command to sniff the scent dispenser after which the animal may perform the defined act that indicates the animal's perception of the scent associated with the disease. If the animal does not perceive the scent associated with the disease, it will not perform the defined act. Finally, the animal's response may be reported to a health care provider.

FIG. 3A illustrates one embodiment of the medical toilet, a scent dispenser, and its use with an animal. In this embodiment, the animal is a dog, although the animal may be another species. Toilet bowl 350 is drawn schematically as a rectangle. Bodily waste sample 310 is schematically represented by an elliptical shape. Bodily waste sample 310 is positioned between blower 315 and scent dispenser 305. When blower 315 is actuated, air moves from blower 315 toward scent dispenser 305 as indicated by the solid arrows. This arrangement results in VOCs 325 emitted from biological waste sample 310 being driven, along with the air, toward scent dispenser 305. VOCs 325 travel through scent dispenser 305 to the environment outside the toilet. There, animal 320 may perceive the scent of VOCs 325.

FIG. 3B illustrates another embodiment of the medical toilet, scent dispenser 305, and its use with animal 320. In this embodiment, the medical toilet comprises receptacle 340. While receptacle 340 is illustrated as a cup, it may contain solid material such as feces. In one embodiment, receptacle 340 contain toilet water or another solvent to at least partially dissolve solid waste and release VOCs 325 from within the solid mass. As with the embodiment of FIG. 3A, blower 315 moves air in the direction illustrated by the solid arrows, over the top of receptacle 340, and through scent dispenser 305. Animal 320 then sniffs VOCs 325 to determine if they contain the disease scent.

FIG. 3C illustrates another embodiment of the medical toilet, scent dispenser 305, and its use with animal 320. In this embodiment, the medical toilet comprises J-tube 330. J-tube 330 is bent with a lower end and an upper end. In this embodiment, the lower end of J-tube 330 is positioned below the surface of toilet water 335. The upper end of J-tube 330 is positioned above the surface of toilet water 335. Bodily waste is deposited into toilet bowl 350 and some or all of the bodily waste is dissolved in toilet water 335. At least some of the dissolved bodily waste enters the lower end of J-tube 330. Through capillary action, the dissolved bodily waste moves through the bottom of J-tube 330 and up through the upper end of J-tube 330. The fluid movement occurs according to the following capillary action formula:

$$h = (2\gamma\theta)/(\mu g r)$$

where h is the height the bodily waste solution moves up the upper end of J-tube 330, $\gamma$ is the liquid-air surface tension (force/unit length), $\theta$ is the contact angle, $\rho$ is the density of the liquid (mass/volume), g is the local acceleration due to gravity (length/divided by the square of time), and r is the radius of J-tube 330.

The diameter of J-tube 330 may be within the range that, according to the capillary action formula, that brings the bodily waste solution to a level that allows VOCs 325 to be drawn out by the air current generated by blower 315 and moved toward scent dispenser 305. Once VOCs 325 travel through scent dispense 305, animal 320 may perceive their scent.

FIG. 4 illustrates an embodiment of the medical toilet that comprises blower 405. In contrast to blower 315 of FIGS. 3A, 3B, and 3C, blower 405 is positioned within toilet bowl 350 adjacent scent dispenser 305. More specifically, blower 405 is positioned between scent dispenser 305 and VOCs 325 that have been emitted from bodily waste. In contrast to blower 315, blower 405 creates negative pressure. Consequently, blower 405 pulls air toward scent dispenser 305 instead of pushing air.

FIG. 5A illustrates an embodiment of a scent dispenser. Sniff dispenser 500 comprises a porous material 505 surrounded by frame 510. Porous material 505 may comprise of a screen with holes of a size that allow VOCs to escape from behind screen 505 but protect blotting sheet 515 from damage that might occur, for example, from the animal's nose touching blotting sheet 515.

Frame 510 surrounds the perimeter of porous material 505 and may be constructed from metal, porcelain, rubber or rubberized materials, plastics that comprise of any of a variety of polymers and copolymers known in the art, glass, silicone, and ceramic. Frame 510 may be constructed of any of a variety of materials that are water resistant so as to not be damaged by exposure to toilet water. Frame 510 may include a gasket constructed of one or more of rubber, rubberized material, plastics that comprise of any of a variety of polymers and copolymers known in the art, or other materials known to prevent liquid leakage.

FIG. 5A further illustrates blotting sheet 515. Frame 520 surrounds the perimeter of blotting sheet 515. Blotting sheet 515 may comprise of any absorbent material, including but not limited to, paper, cotton, polyester, hemp, bamboo, modal fabric, and polyamide. As one of skill in the art will readily understand, any material that absorbs liquid and allows VOCs to escape from the material may be used to manufacture blotting sheet 515.

Frame 510 may be constructed to receive and hold frame 520, frame 520 being in combination with blotting sheet 515, such that blotting sheet 515 is positioned behind porous material 505. In one embodiment, frames 510 and 520 are constructed so that frame 520 is a cassette that slides laterally to a position within frame 510 fits within frame 510. FIG. 5B provides a side view of frame 520 positioned within frame 510 in an embodiment of a medical toilet in accordance with the disclosed invention.

Blotting sheet 515 may be positioned within the medical toilet, such that toilet water or other solvent comes in physical contact with at least a part of blotting sheet 515 when a user has deposited bodily waste into the toilet. Alternatively, blotting sheet 515 may be positioned such that liquid bodily waste comes directly in physical contact with blotting sheet 515 without being diluted by solvent. For example, the user's urine stream may come in contact with blotting sheet 515.

In either scenario, blotting sheet 515 wicks the solution or liquid bodily waste so that it is spread across blotting sheet 515. VOCs evaporate into the environment outside the toilet, traveling through porous material 505. The animal is then able to smell the VOCs to assess them for the disease scent.

FIG. 5B illustrates yet another embodiment of the invention which incorporates the scent dispenser of FIG. 5A. In addition, the embodiment of FIG. 5B comprises a receptacle 525 which is in connection with pipe 530. Similar to receptacle 340 of FIG. 3B, receptacle 525 is positioned to receive bodily waste which the user deposits through the hole in seat 120. Receptacle 525 may be above or below the surface of the toilet water. In embodiments in which receptacle 525 is positioned below the surface of the toilet water, bodily waste, including solid waste, may be dissolved by the toilet water. Alternatively, other solvents may be present in receptacle 525 which may dissolve solid waste.

The bodily waste, which may or may not be dissolved in a solvent, travels through pipe 530 toward the scent dispenser. Blotting sheet 515 extends from frame 520 such that it is in contact with the interior of the end of pipe 530. The liquid bodily waste or bodily waste solution is wicked up into and throughout blotting sheet 515. VOCs evaporate from blotting sheet 515, travel through porous material 505, and into the environment outside of the medical toilet. The animal is then able to smell the VOCs to assess them for the disease scent.

FIG. 5C is another embodiment of a scent dispenser according to the disclosed invention. Concentrator 540 is a cone-shaped embodiment of a scent dispenser which funnels VOCs 325 into a smaller space. VOCs 325 emerge from the smaller end of concentrator 325. VOCs 325 move in the direction of the solid arrows shown in FIG. 5C. The volume of room air occupied by the VOCs 325 is smaller so the animal receives a more concentrated gas stream. One or more of the blowers disclosed herein may be used to provide force to move VOCs 325 through concentrator 540.

Figure 6A:
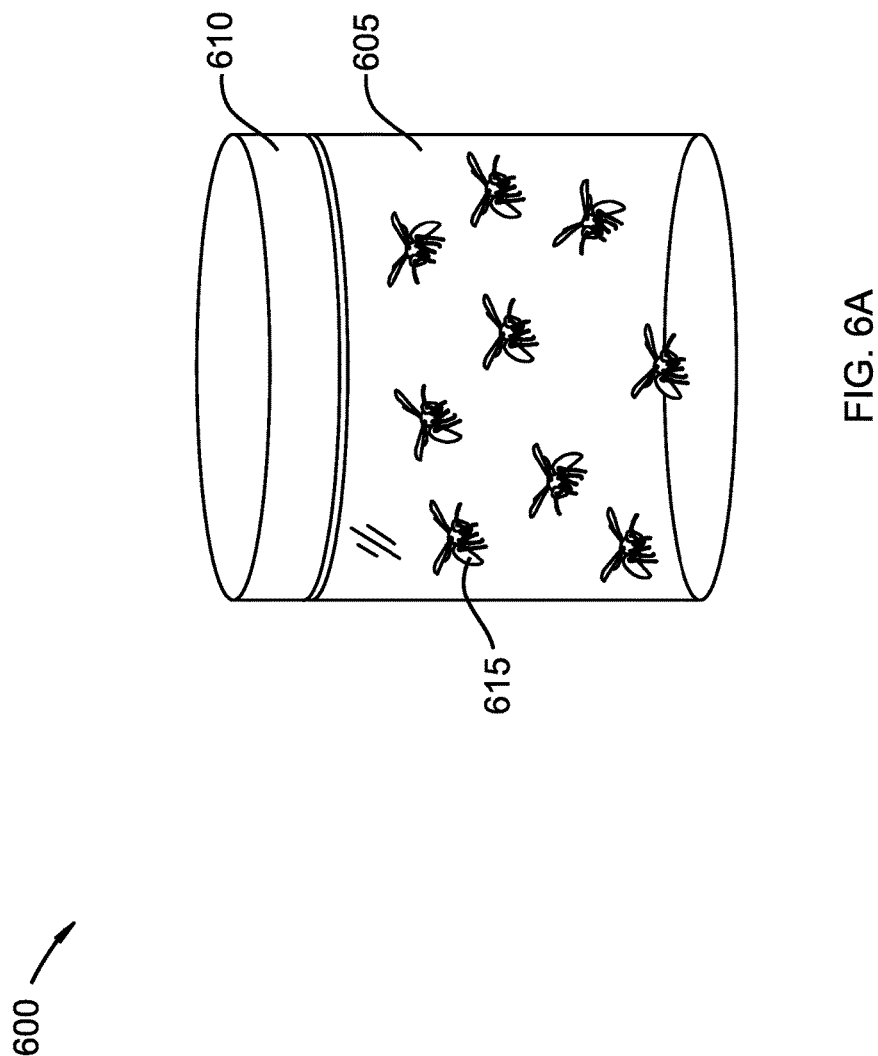
FIG. 6A is a canister containing insects, the canister being a part of an embodiment of the scent dispenser in accordance with an embodiment of the invention.

While FIGS. 3A, 3B, and 3C illustrate a dog, FIG. 6A illustrates an embodiment in which insects 615 identify the scent associated with bodily waste collected from a diseased user. FIG. 6A illustrates container 605 which may be a canister or other enclosure that will contain live insects. One end of container 605 includes attachment device 610 which functions similar to frame 510 of FIG. 5A. Attachment device 610 may include a porous material that covers the end of container 605 and allows VOCs 325 to enter container 605. Insects 615 smell VOCs 325 as they enter container 605. Like the embodiment in which the animal comprises a dog, insects 615 have been trained to differentiate between the scent of bodily waste from a user that is afflicted with a defined disease from bodily waste from a user that is not afflicted with the disease. Also, insects 615 respond by performing a defined act that signals to an observer when insects 615 have perceived the scent associated with the disease.

Figure 6B:
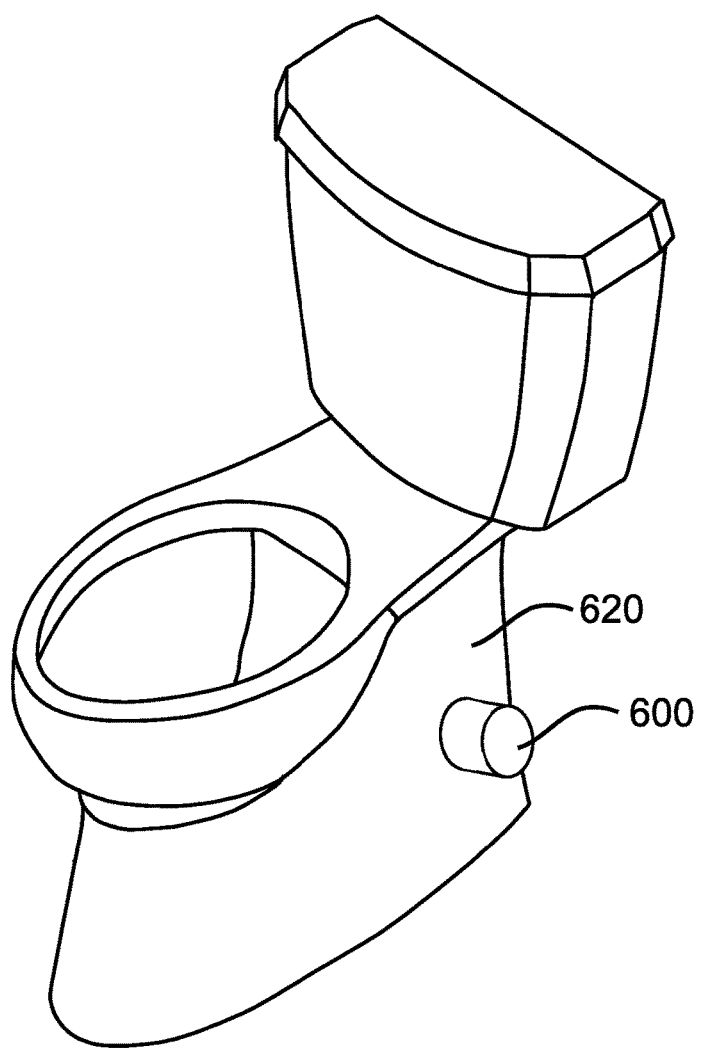
FIG. 6B is a perspective view of a medical toilet with the canister of FIG. 6A mounted on the toilet.

FIG. 6B illustrates the container 605 of FIG. 6A as it appears when attached to toilet 620 which is an embodiment of the medical toilet disclosed herein. Similar to other embodiments of the scent dispenser, container 605 attaches to toilet 620 on a side of toilet 620. Container 605 is in communication with the toilet bowl of toilet 620.

Figure 7:
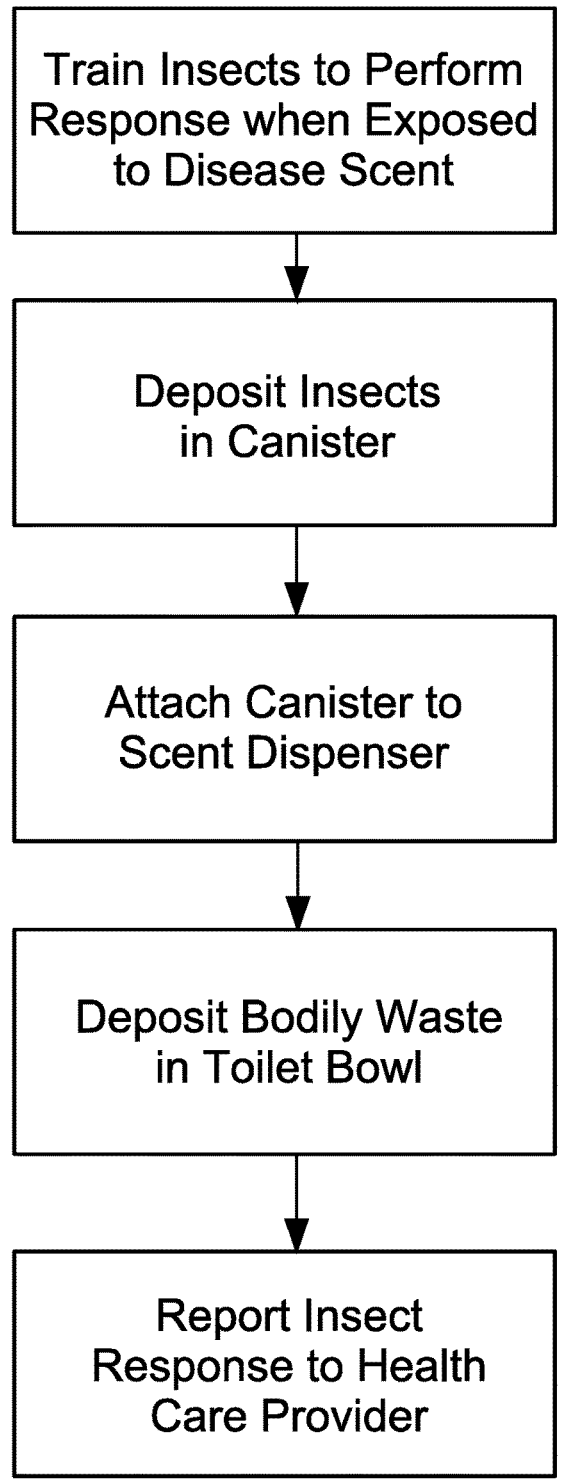
FIG. 7 is a flow chart illustrating a method of using the medical toilet of FIG. 6B with the canister of FIG. 6A mounted on it.

FIG. 7 is a flow chart that illustrates an embodiment of a method in which container 605 and insects 615 may be used in accordance with the disclosed invention. Insects 605 may be trained to perform a defined act when they are exposed to the scent of bodily waste that was collected from a user afflicted with a defined disease. The defined act may comprise of one or more of vibrating, extending a proboscis, increased movement, emitting a sound whether or not the sound is audible by the human ear. One of skill in the art will understand that other insect behaviors may indicate perception of the disease scent by insects 615.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of diagnosing a disease in a user comprising the steps of:
   providing a toilet, the toilet comprising:
   a toilet bowl;
   a toilet seat;
   a scent dispenser, the scent dispenser comprising:
   an opening within a side of the toilet;
   wherein the opening is defined by a frame, the frame comprising a first side in communication with an environment outside the toilet bowl and a second side in communication with an environment inside the toilet bowl;
   wherein the opening connects the environment inside the toilet bowl with the environment outside the toilet bowl; and
   wherein the opening defines a conduit to transfer volatile organic compounds from the toilet bowl to the environment outside the toilet; and
   a blower, wherein the blower is positioned within the toilet bowl and opposite the scent dispenser;
   providing an animal, wherein the animal is trained to:
   smell the air being emitted from the scent dispenser;
   identify a scent that is associated with a defined disease; and
   perform a defined act when the animal perceives scent associated with the disease; and
   depositing bodily waste from the user into the toilet bowl, wherein the bodily waste emits volatile organic compounds; and
   signaling the animal to sniff the scent dispenser and perform the defined act when the animal perceives the scent associated with the disease.

2. The method of claim 1, wherein the toilet further comprises a bodily waste receptacle, wherein the bodily waste receptacle is positioned inside the toilet bowl, below the toilet seat, between the blower and the scent dispenser, and wherein at least a portion of the bodily waste is deposited into the bodily waste receptacle during the step of depositing bodily waste from the user into the toilet bowl.

3. The method of claim 1, wherein the toilet further comprises a J-shaped tubing:
   wherein the J-shaped tubing comprises an upper end and a lower end;
   wherein the J-shaped tubing is positioned within the toilet bowl;
   wherein the upper end of the J-shaped tubing is located proximate to the second side of the frame;
   wherein the lower end of the J-shaped tubing is positioned below the surface of the toilet water;
   wherein a solution comprising toilet water and bodily waste enters the lower end of the J-shaped tubing; and
   wherein the solution is elevated within the J-shaped tubing through capillary action to a level that is above the surface of the toilet water.

4. A method of diagnosing a disease in a user, wherein the disease is associated with a disease process that causes the user to excrete bodily waste comprising at least one volatile organic compound that is not detectable by smell in users not afflicted with the disease, the method comprising the steps of:
   providing a toilet, the toilet comprising:
   a toilet bowl, the toilet bowl housing a volume of toilet water;
   a toilet seat;
   a scent dispenser, the scent dispenser comprising:
   an opening within a side of the toilet;
   wherein the opening is defined by a frame, the frame comprising a first side in communication with an environment outside the toilet bowl and a second side in communication with an environment inside the toilet bowl;
   wherein the opening connects the environment inside the toilet bowl with the environment outside the toilet bowl; and wherein the opening defines a conduit to transfer volatile organic compounds from the environment inside the toilet bowl to the environment outside the toilet; and a blower, wherein the blower is positioned within the toilet bowl and opposite the scent dispenser;

providing an animal, wherein the animal is trained to:
  identify a scent that is associated with a defined disease; and
  perform a defined act when the animal perceives the scent associated with the disease;

depositing bodily waste from the user into the toilet bowl, wherein the bodily waste emits volatile organic compounds; and signaling the animal to sniff the scent dispenser and perform the defined act when the animal perceives the scent associated with the disease.

5. The method of claim 4, wherein the toilet further comprises a bodily waste receptacle, wherein the bodily waste receptacle is positioned inside the toilet bowl, below the toilet seat, and between the blower and the scent dispenser, and wherein at least a portion of the bodily waste is deposited into the bodily waste receptacle during the step of depositing bodily waste from the user into the toilet bowl.

6. The method of claim 4, wherein the toilet further comprises a J-shaped tubing:
  wherein the J-shaped tubing comprises an upper end and a lower end;
  wherein the J-shaped tubing is positioned within the toilet bowl;
  wherein the upper end of the J-shaped tubing is located proximate to the second side of the frame;
  wherein the lower end of the J-shaped tubing is positioned below the surface of the toilet water;
  wherein a solution comprising toilet water and bodily waste enters the lower end of the J-shaped tubing; and
  wherein the solution is elevated within the J-shaped tubing through capillary action to a level that is above the surface of the toilet water.

* * * * *